(12) United States Patent
Maier et al.

(10) Patent No.: US 7,239,383 B2
(45) Date of Patent: Jul. 3, 2007

(54) METHOD AND APPARATUS FOR SPECTRAL MODULATION COMPENSATION

(75) Inventors: John S. Maier, Pittsburgh, PA (US); Jason N. Neiss, Pittsburgh, PA (US); Shona Stewart, Pittsburgh, PA (US); Matthew P. Nelson, Harrison City, PA (US); Joseph Demuth, Pittsburgh, PA (US); Patrick J. Treado, Pittsburgh, PA (US)

(73) Assignee: Chemimage Corporation, Pittsburgh, PA (US)

( * ) Notice: Subject to any disclaimer, the term of this patent is extended or adjusted under 35 U.S.C. 154(b) by 319 days.

(21) Appl. No.: 10/879,632

(22) Filed: Jun. 30, 2004

(65) Prior Publication Data

US 2006/0001867 A1    Jan. 5, 2006

(51) Int. Cl.
    *G01J 3/44*    (2006.01)
(52) U.S. Cl. ................................. 356/301; 356/307
(58) Field of Classification Search ................ 356/301, 356/224, 246, 307; 382/133, 134
    See application file for complete search history.

(56) References Cited

U.S. PATENT DOCUMENTS

| | | |
|---|---|---|
| 4,660,151 A | 4/1987 | Chipman et al. |
| 4,701,838 A | 10/1987 | Swinkels et al. |
| 4,766,551 A | 8/1988 | Begley |
| 4,885,697 A | 12/1989 | Hubner |
| 5,072,338 A | 12/1991 | Hug et al. |
| 5,121,337 A | 6/1992 | Brown |
| 5,121,338 A | 6/1992 | Lodder |
| 5,124,932 A | 6/1992 | Lodder |
| 5,311,445 A | 5/1994 | White |
| 5,324,567 A | 6/1994 | Bratchley et al. |
| 5,481,476 A | 1/1996 | Windig |
| 5,510,894 A * | 4/1996 | Batchelder et al. ......... 356/301 |
| 5,606,164 A | 2/1997 | Price et al. |
| 5,610,836 A | 3/1997 | Alsmeyer et al. |
| 5,710,713 A | 1/1998 | Wright et al. |
| 5,751,415 A | 5/1998 | Smith et al. |
| 5,822,219 A | 10/1998 | Chen et al. |
| 6,002,476 A | 12/1999 | Treado |
| 6,008,888 A | 12/1999 | Nottke et al. |
| 6,239,904 B1 | 5/2001 | Serfling et al. |
| 6,306,589 B1 * | 10/2001 | Muller et al. .................. 435/6 |
| 6,485,981 B1 | 11/2002 | Fernandez |
| 6,549,861 B1 | 4/2003 | Mark et al. |
| 6,584,413 B1 | 6/2003 | Keenan et al. |

(Continued)

OTHER PUBLICATIONS

Conti, S., et al., "Traces of Polymethylsiloxane in case histories of rape: technique for detection," Elsvier Science Ireland Ltd, Forensic Science International, Jan. 1995, pp. 121-128.

(Continued)

*Primary Examiner*—Tarifur Chowdhury
*Assistant Examiner*—Marissa J. Detschel
(74) *Attorney, Agent, or Firm*—Duane Morris LLP

(57) ABSTRACT

The embodiments disclosed herein generally relate to identifying and removing background noise in spectroscopic imaging of a sample. Because white-light has essentially constant intensity at every wavelength, background noise caused by white light can be identified and removed from spectroscopic measurements including Raman spectroscopy. Thus, once the Raman spectrum for a sample is obtained, it may be corrected to remove the white-light dispersive spectrum in accordance with the embodiments disclosed herein.

70 Claims, 4 Drawing Sheets

U.S. PATENT DOCUMENTS 6,939,686 B2 * 9/2005 Ling et al. .................... 435/29

OTHER PUBLICATIONS

Lee, G.S.H., et al., "A Methodology Based on NMR Spectroscopy for the Forensic Analysis of Condoms," St. Andrews Centre for Advanced Materials, pp. 808-821.

Maynard, P., et al., "A protocol for the forensic analysis of condom and personal lubricants found in sexual assault cases," Forensic Science International, 124 (2001), pp. 140-156.

Stoilovic, M., et al., "The Application of Light in Forensic Science & A Modern Approach to Fingerprint Detection and Enhancement," Australian Federal Police, AFP Workshop Manual, Oct. 2000.

Roux, C., et al., "Evaluation of 1,2-Indanedione and 5,6-Dimethoxy-1,2-Indanedione for the Detection of Latent Fingerprints on Porous Surfaces," Journal of Forensic Sciences, vol. 45(4), 2000, pp. 761-769.

Roux, C., et al., "A study to investigate the evidential value of blue and black ballpoint pen inks in Australia," Forensic Science International, 101 (1999), pp. 167-176.

Mazzella, W.D., et al., "Classification and Identification of Photocopying Toners by Diffuse Reflectance Infrared Fourier Transform Spectroscopy (DRIFTS): I. Preliminary Results," Journal of Forensic Sciences, JFSCA, vol. 36, No. 2, Mar. 1991, pp. 449-465.

Mazzella, W.D., et al., "Classification and Identification of Photocopying Toners by Diffuse Reflectance Infrared Fourier Transform Spectroscopy (DRIFTS): II. Final Report," Journal of Forensic Sciences, JFSCA, vol. 36, No. 3, May 1991, pp. 820-837.

Brunelle, R.L., "Questioned Document Examination," Bureau of Alcohol, Tobacco, and Firearms, U.S. Treasury Department, 1982.

Robertson, J., et al., "The Persistence of Textile Fibres Transferred During Simulated Contacts," Journal of Forensic Sciences, vol. 22, No. 4, Oct. 1982, p. 353-360.

Gaudette, B.D., "The Forensic Aspects of Textile Fiber Examination," Central Forensic Laboratory, Royal Canadian Mounted Police.

Pounds, C.A., et al., "The Transfer of Fibres between Clothing Materials During Simulated Contacts and their Persistence During Wear: Part I—Fibre Transference," Journal of Forensic Sciences, vol. 15, 1975, pp. 17-27.

Pounds, C.A., et al., "The Transfer of Fibres between Clothing Materials During Simulated Contacts and their Persistence During Wear: Part II—Fibre Persistence," Journal of Forensic Sciences, vol. 15, 1975, pp. 29-37.

Maynard, P., et al., "Adhesive Tape Analysis: Establishing the Evidential Value of Specific Techniques," Journal of Forensic Sciences, vol. 46(2), 2001, pp. 280-287.

Caetano, M.R., et al., "Evaluation of the importance of non-linear spectral mixing in coniferous forests," EUROPTO Conference on Remote Sensing for Agriculture, Ecosystems, and Hydrology, Barcelona, Spain, Sep. 1998.

Rasmussen, G.T., et al., "Library Retrieval of Infrared Spectra Based on Detailed Intensity Information," Applied Spectroscopy, vol. 33, No. 4, 1979.

Guilment, J., et al., "Infrared Chemical Micro-Imaging Assisted by Interactive Self-Modeling Multivariate Analysis," Applied Spectroscopy, vol. 48, No. 3, 1994.

* cited by examiner

METHOD AND APPARATUS FOR SPECTRAL MODULATION COMPENSATION

The instant specification relates to application Ser. Nos. 10/879,633 and 10/879,636 filed concurrently on 30 Jun. 2004 herewith and entitled, respectively, "System and Method for spectroscopy and Imaging" and "Method and Apparatus for Dark Field Chemical Imaging". Each of said application is incorporated herein in its entirety.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscopes or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors, a type of FPA, are typically employed with visible wavelength fluorescence and Raman spectroscopic imaging systems, while indium gallium arsenide (InGaAs) FPA detectors are typically employed with near-infrared spectroscopic imaging systems.

A variety of imaging spectrometers have been devised for spectroscopic imaging systems. Examples include, without limitation, grating spectrometers, filter wheels, Sagnac interferometers, Michelson interferometers and tunable filters such as acousto-optic tunable filters (AOTFs) and liquid crystal tunable filters (LCTFs).

A number of imaging spectrometers, including AOTFs and LCTFs are polarization sensitive, passing one linear polarization and rejecting the orthogonal linear polarization. As a result, theoretical efficiency is 50%. Practical efficiency is reduced due to scattering losses, imperfect spectrometer action, absorption losses in polarizing optics, etc. Practical efficiency of 30% peak transmittance or less is more typical. Previous spectroscopic imaging instruments accepted the optical losses associated with polarization sensitive imaging spectrometers.

The efficiency of imaging spectrometers is also a function of the system-specific noise caused by background light. For example, the LCTF has a wavelength dependent transmission modulation which affect's the accuracy and the efficiency of measuring sharp Raman bands with weak Raman scatterers. Experiments with certain LCTF devices show complicated interactions arising in the material and structure of the imaging devices produce a spatial and spectral modulation of light coming through the imaging device. The modulation produces an apparent background signal that is not uniform and masks the real signal. Much of the background noise has comparable structural features (e.g., peak width) as the Raman signal. For material having weak Raman scattering or samples having a low concentration of the material being studied, the background noise can mask or obscure the real signal. Because the ability to detect Raman vibrational features on a uniform background is critical to identifying small signal levels, the background noise can have a detrimental affect on the spectral detection.

SUMMARY OF THE DISCLOSURE

According to one embodiment, the disclosure relates to a method for obtaining a corrected spectrum of a sample, the method including illuminating the sample with a first light source having a substantially constant intensity at each wavelength of a predetermined wavelength band to thereby obtain a white-light spectral image of the sample; illuminating the sample with a second light source at each wavelength of the predetermined wavelength band to thereby obtain an initial spectrum of the sample; and filtering the initial spectrum to substantially remove the white-light spectral image from the initial spectrum to thereby obtain a corrected spectrum of the sample. In one embodiment, the laser light source can be replaced by a light source having sufficiently narrow bandwidth to distinguish the Raman scattered light from the sample.

A Raman image is also referred to herein as a spatially accurate wavelength-resolved image and is an image of a sample that is formed from multiple "frames" wherein each frame has plural spatial dimensions and is created from photons of a particular wavelength (or wave number) or from photons in a particular wavelength band (or wave number band) so that the frames may be combined to form a complete image across all wavelengths (or wave numbers) of interest.

In another embodiment, the disclosure is directed to an apparatus for refining the Raman image of a sample, the apparatus having a processor programmed to receive a first spectral image of the sample, the first spectral image providing a spectral intensity distribution of the sample under illumination by a plurality of wavelengths having substantially similar intensity; receive a second spectral image of the sample, the second spectral image providing the spectral intensity distribution of the sample illuminated by one wavelength; and manipulate the second spectral image of the sample by substantially removing the first spectral image therefrom to form a refined Raman image. Each of the first or the second spectral image may include a single pixel at multiple wavelengths.

In still another embodiment, the disclosure is directed to a method for obtaining a refined Raman image of a sample by obtaining a first spectral image of the sample by illuminating the sample at one wavelength and measuring the intensity of scattered photons from the sample at all wavelengths; obtaining a second spectral image of the sample by illuminating the sample simultaneously with a plurality of visible wavelengths and measuring intensity of scattered photons from the sample at the plurality of wavelengths and filtering the first spectral image by substantially removing the second spectral image to form the refined Raman image.

In yet another embodiment, the disclosure is directed to a system and method for obtaining a spectrum of a sample, including a Raman spectrum and/or a spatially accurate wavelength-resolved image, where the sample is placed on a substrate that is coated with a material that does not emit Raman scattered photons when exposed to illuminating photons. Such a coating may be metal and may be preferably aluminum. Additionally, the substrate may have an optically smooth surface and may be a microscope slide.

DETAILED DESCRIPTION

The embodiments disclosed herein enable better detection and clearer images from spectroscopic imaging than conventionally possible. Application of Raman spectroscopy with certain biomedical samples including cells, tissues, bacteria, viruses and other biological entities result in weak Raman scattering. The embodiments disclosed herein enable detecting such samples when they are present at low concentrations.

Virtually all spectral imaging filters such as AOTF, LCTF, AOF depend on the optical properties and transmission of light through one or more optical devices in order to produce the desired filtering effect. The filters have complex internal configuration which affects transmission of light through the device creating a background noise having a grass-like appearance on the final image. Although the imaging filters are designed to minimize background noise, residual effects remain which limit the use of these filters for sensitive applications. In particular, for small sample concentration or for weak Raman scattering material, these effects render the filters impractical.

Additionally, the material upon which the sample may be placed may negatively impact the spectrum or image of the sample that is being obtained. It shall be understood by those of skill in the art that the spectrum may be a spectroscopic spectrum, a Raman spectrum, or a spatially accurate wavelength-resolved image. The negative impact may be minimized by placing the sample on a substrate that is coated with a material that does not emit Raman scattered photons when exposed to illuminating photons. Such a coating may be metal and may be preferably aluminum. Additionally, the substrate may have an optically smooth surface and may be a microscope slide.

Figure 1:
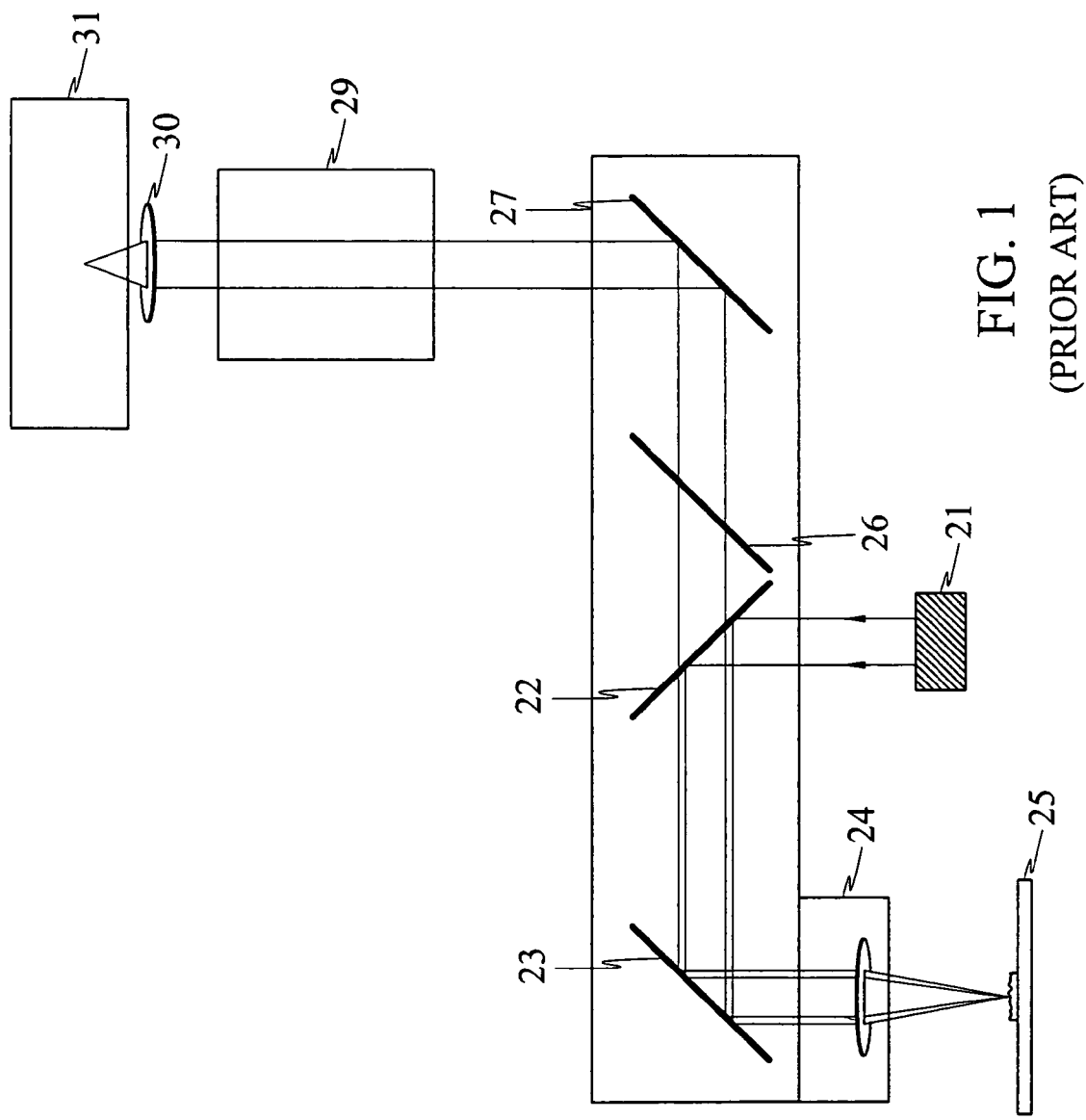
FIG. 1 is a schematic representation of a conventional Raman imaging system.

FIG. 1 is a schematic representation of a conventional Raman imaging system. Referring to FIG. 1, sample 25 is placed on a slide within the purview of objective lens 24. Light source 21 (i.e., laser) provides illumination to sample 25 vis-à-vis the beam-splitter 22 and the mirror 23. The mirror 23 is also positioned to receive and redirect the sample's image in the form of scattered photons emanating from sample 25 to mirror 27. The beam-splitter 22 may include a 50/50 beam-splitter, a dielectric interference, a dichroic beam-splitter, or a holographic optical filter. Optionally laser rejection filter 26 may be placed between beam-splitter 22 and mirror 27 to remove the laser light while transmitting other wavelengths of the optical beam directed through beam-splitter device 22. Laser rejection filter 26 may include a dielectric interference filter, a holographic optical filter or a rugate optical filter. The scattered photons are then directed to tunable filter 29 and then to the focal plane array (FPA) device 31 through lens 30. The FPA may include silicon charge-coupled device (CCD) detector, charge-injection device (CID) detector or infrared FPA.

The light entering tunable filter 29 is not limited to the Raman scattered photons from image 25. Instead, the light entering filter 29 includes background photons which will affect the quality of the Raman image. Experiments with certain LCTF devices show that complicated interactions arising in the material and the imaging device can produce a spatial and spectral modulation of light going through the imaging device. The additional photons (i.e., the white-light) produce an apparent background signal that is not uniform and masks the real signal. The background signal is instrument-specific and varies even among tunable filters of the same specification. Much of the background noise has structural features (e.g., peak width) comparable to the Raman signal.

Figure 2:
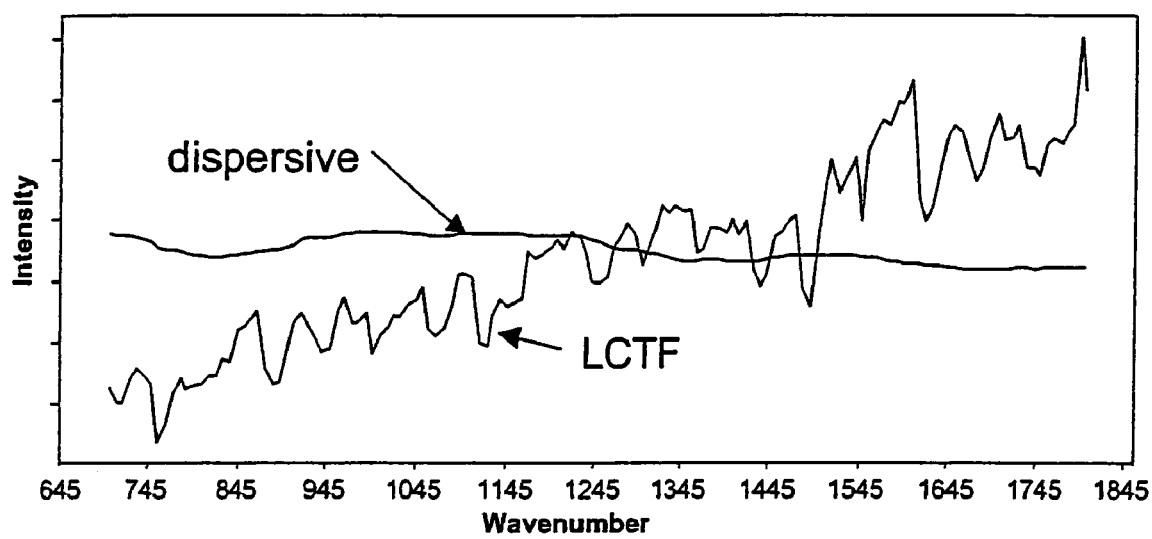
FIG. 2 shows the effect of white-light spectrum through an LCTF and a dispersive spectrometer.

FIG. 2 shows the effect of white-light spectrum through a LCTF and a dispersive spectrometer. For reference the dispersive spectrum of white-light on the instrument is also shown. The modulating effect of white-light on the LCTF spectrum is evident over the same fingerprint or focal plane (FP) region.

Figure 3:
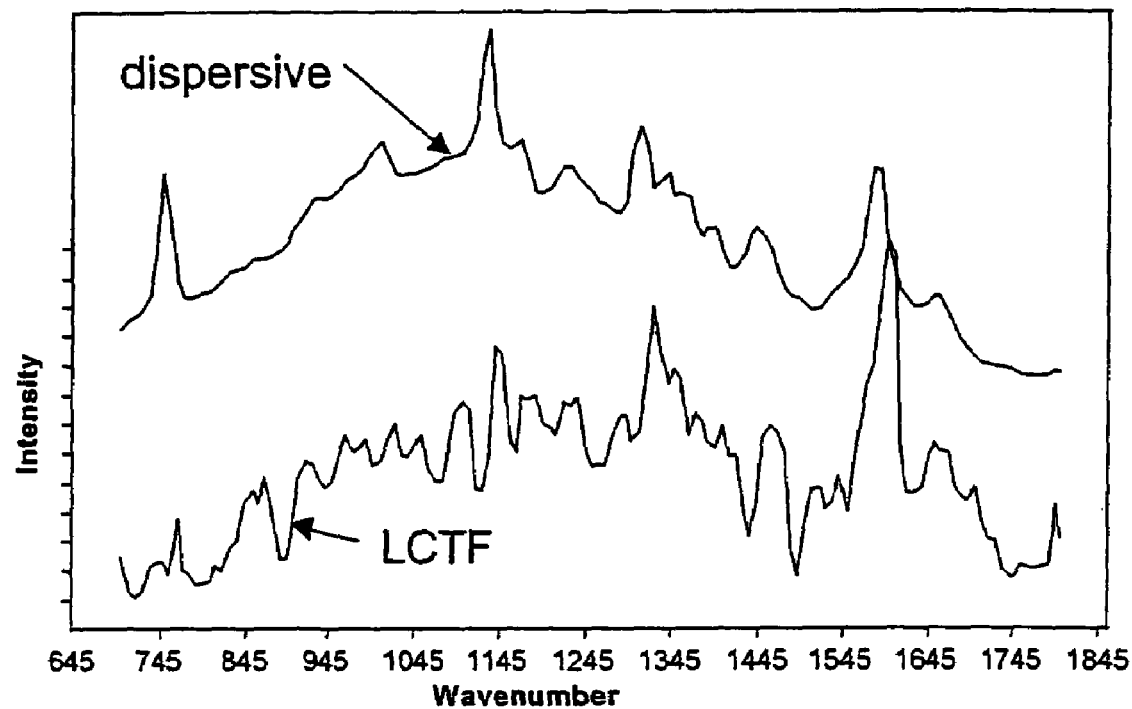
FIG. 3 shows the Raman Spectrum from an LCTF Raman image and a dispersive spectrum for the same field of view.

FIG. 3 shows the Raman Spectrum from an LCTF Raman image and a dispersive spectrum for the same field of view. Specifically, FIG. 3 compares the FP region spectrum from a sample. The similarities between the noise in the LCTF spectrum and the white-light spectrum can be readily seen.

In one embodiment of the disclosure, the instrument-specific response of the filter is measured against a white-light spectrum and used to calibrate the apparatus and remove the non-uniform spectral and spatial background effects. Such instrument specific response detection enables higher-sensitivity and clearer images for stereoscopic imaging than are conventionally possible. Thus, according to one embodiment, the disclosure is directed to a method for filtering a spectrometric image of a sample by illuminating the sample with a light source. The light source may have a substantially uniform intensity at all wavelengths to obtain a first spectral image of the sample. The light source having substantially uniform intensity at all wavelengths can be a white light. Next, the sample is illuminated with a laser light source to obtain an initial Raman image of the sample. By filtering the initial Raman spectrum of the sample to remove the white-light spectrum therefrom, a final Raman image of the sample can be obtained.

Although any photonic source capable of providing a single wavelength can be used for this purpose, a laser source may be particularly suitable. For example, the laser light source may have a wavelength in the range of about 500-800 nm, or alternatively, in the range of about 280-1200 nm. Moreover, the step of illuminating the sample with the laser light source may include forming an initial Raman image from a plurality of photons scattered by the sample. As stated, the initial Raman image may include background noise stemming from the apparatus-specific reactions to white-light.

Assuming that a white-light source has essentially constant intensity at all wavelengths, the wavelength-dependent transmission factors of the optics (including the instrument-specific response of the LCTF) can be removed from the data by manipulating the measured spectrum by the white-light spectrum to recover the spectral features from the dispersive spectrum.

Figure 4:
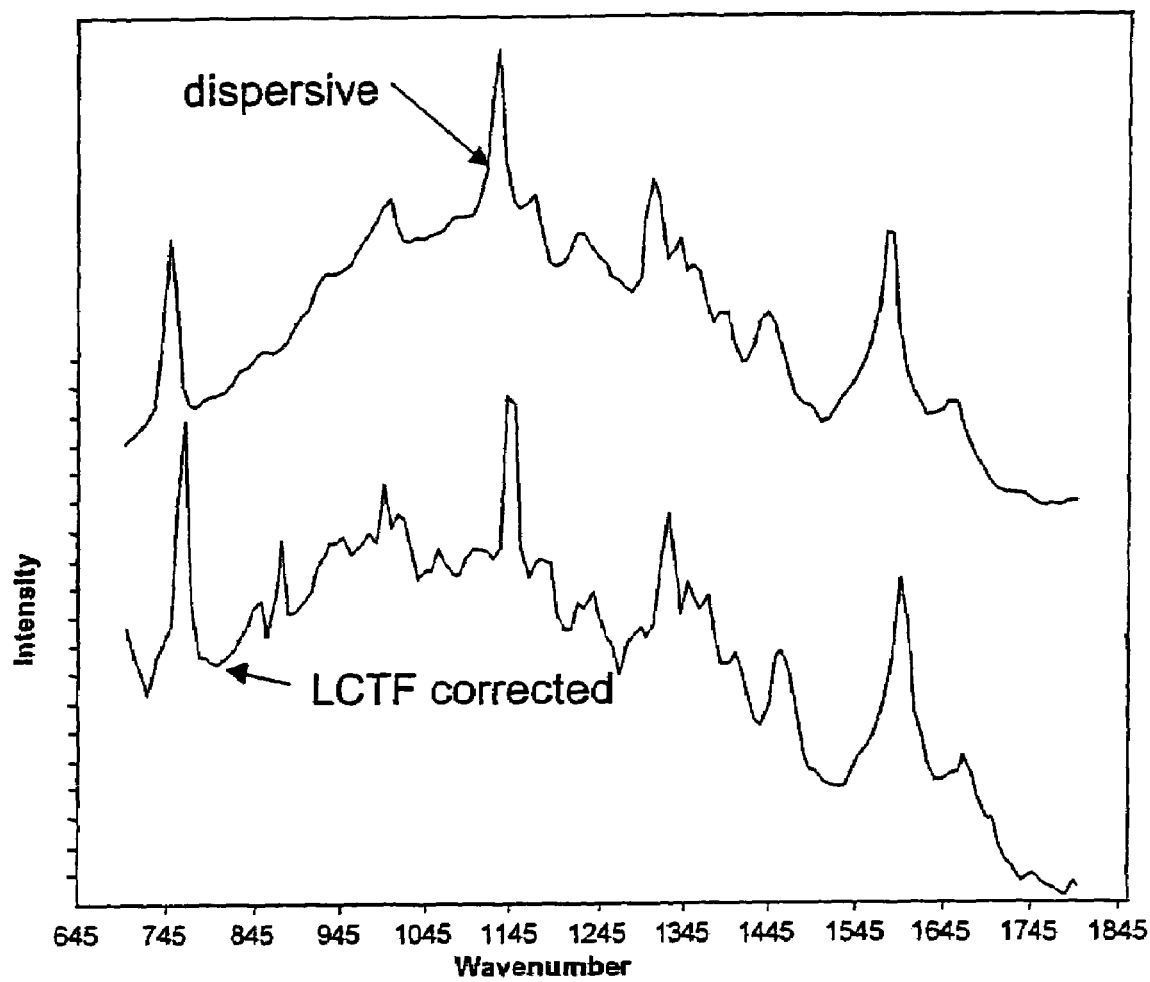
FIG. 4 shows a corrected spectrum matching the dispersive spectrum.

FIG. 4 shows a corrected spectrum matching the dispersive spectrum according to one embodiment of the disclosure. In the representative embodiment of FIG. 4, LCTF Raman spectrum is corrected by dividing the initial spectrum by the white-light LCTF image. The dispersive spectrum is shown in FIG. 4 for reference. The apparent shift of the peaks in the dispersive spectrum relative to the LCTF spectrum are due to offsets in the LCTF independent of this effect. The shift of the peaks in the dispersive spectrum relative to the LCTF spectrum are due to offsets in the LCTF independent of this effect.

In order to filter out the instrument-specific background noise from the initial Raman image in accordance with one embodiment of the disclosure, the initial Raman image can be divided by the white-light spectrum of the sample. Alternatively, the white-light spectral image of the sample can be subtracted from the initial Raman image. In addition to filtering, the final Raman image may be mathematically normalized to provide the desired sharpness and definition. Thus, the final Raman image can be substantially free from background interference.

According to another embodiment, the disclosure relates to a method for obtaining a Raman image of a sample by illuminating the sample with a light source having similar intensity at all wavelengths to obtain a white-light spectral image of the sample ("the first spectrum"). While the light source having similar intensity at all wavelengths can be a white-light with substantially similar intensities at all visible wavelengths, the scope of the disclosure is not limited thereto. The white-light spectrum of the sample can be formed by collecting individual spectra of the sample as a function of the wavelength to form a spectrum of the sample.

Next the sample is illuminated with a light source having narrow bandwidth sufficient to distinguish Raman scattered light from the sample and define an initial Raman spectrum of the sample ("the second spectrum"). This step can be performed by using a conventional tunable filter such as those discussed above. The light source having a narrow bandwidth can be a laser light source. Thus, a laser would illuminate the sample. The scattered photons from the sample would then be collected by an objective lens or other similar optical devices which direct the scattered photons to a tunable filter and an image processing device for forming the initial Raman spectrum. The initial Raman spectrum of the sample may include background noise that distort the accuracy and the sharpness of the Raman image.

To address this problem, the initial Raman spectrum can be filtered to substantially remove the white-light spectral image of the sample from the first Raman spectrum and to form a final Raman image of the sample. The filtering step may be accomplished by of subtracting the first spectrum from the second spectrum, or alternatively by dividing the second spectrum by the first spectrum.

An apparatus according to an embodiment of the disclosure may include a processor programmed to receive a first spectral image of the sample. The first spectral image of the sample can be formed by illuminating the sample with white-light. Next, a second spectral image of the sample may be directed to the processor. The second spectral image can be obtained as outlined above, for example, by illuminating the sample with a laser source and obtaining its initial Raman image.

The processor may optionally align the first and the second images before proceeding with the filtering step. This step can be performed by aligning the images along a common wavelength.

Because the initial Raman image conventionally includes the background noise described above, the processor may manipulate the second spectral image by removing the first spectral image and form a refined Raman image. The processor may further normalize the refined image to produce a clearer image. The normalization process may include normalizing the first spectral image at each pixel; blurring the first spectral image at each wavelength; and at each wavelength dividing the second spectral image by the first spectral image. Other conventionally known normalization steps may be implemented without departing from the principles disclosed herein.

To enable rapid processing of these steps, the processor may be coupled to one or more database. For example, a first database can store the apparatus-specific response to white-light. Thus, the processor receives the initial Raman image, the processor may then search the first database and retrieve a corresponding first spectral image of the sample or a spectral image corresponding to the equipment being used. In addition, a storage medium can be provided to store the final Raman image or any image relating to the sample. Finally, network interface devices such as a monitor or a printer can be used for communicating the results.

Although the disclosure has been described with reference to specific exemplary embodiments discussed and illustrated herein, it should be noted that the principles of the disclosure are not limited thereto and include any permutation or modification thereto.

What is claimed is:

1. A method for producing a spectrum of a sample comprising:
   providing a sample;
   providing illuminating photons;
   receiving photons scattered by said sample when illuminated by said illuminating photons to thereby produce collected photons wherein the collected photons include Raman scattered photons and non-Raman scattered photons;
   receiving said collected photons and passing ones of said collected photons having a wavelength in a predetermined wavelength through a tunable filter to thereby produce imaging photons;
   detecting said imaging photons with a photon detecting device; and
   compensating for detecting said non-Raman scattered photons as a function of the imaging photons and the non-Raman scattered photons to thereby produce a spectrum of the sample.

2. The method of claim 1 wherein the spectrum is a Raman spectrum.

3. The method of claim 1 wherein the spectrum is a spatially accurate wavelength-resolved image.

4. The method of claim 1 wherein the step of compensating for detecting said non-Raman scattered photons further comprises the steps of:
   determining the intensity of the non-Raman scattered photons detected by the photon detecting device for each of a plurality of wavelengths; and
   for one of the plurality of wavelengths, dividing the intensity of the imaging photons at said one wavelength by the intensity of the non-Raman scattered photons at said one wavelength.

5. The method of claim 1 wherein the step of compensating for detecting said non-Raman scattered photons further comprises the steps of:
   determining the intensity of the non-Raman scattered photons detected by the photon detecting device for each of a plurality of wavelengths; and
   for one of the plurality of wavelengths, subtracting the intensity of the non-Raman scattered photons at said one wavelength from the intensity of the imaging photons at said one wavelength.

6. The method of claim 1 wherein the step of compensating for detecting said non-Raman scattered photons further comprises the steps of:
determining the intensity of the non-Raman scattered photons detected by the photon detecting device for each of a plurality of wavelengths; and
for one of the plurality of wavelengths, mathematically normalizing the intensity of the imaging photons at said one wavelength as a function of the intensity of the non-Raman scattered photons at said one wavelength.

7. The method of claim 1 wherein the step of providing the sample includes providing the sample on a substrate coated with a material that does not emit Raman scattered photons when illuminated by said illuminating photons.

8. The method of claim 7 wherein the step of providing the sample includes providing the sample on a substrate coated with metal.

9. The method of claim 8 wherein the step of providing the sample includes providing the sample on a substrate coated with aluminum.

10. The method of claim 7 wherein the substrate has an optically smooth surface.

11. The method of claim 7 wherein the substrate is a microscope slide.

12. A method for producing a spectrum of a sample comprising:
providing a sample;
providing illuminating photons;
receiving photons scattered by said sample when illuminated by said illuminating photons to thereby produce collected photons wherein the collected photons include Raman scattered photons and non-Raman scattered photons;
receiving said collected photons at a tunable filter and blocking ones of said collected photons having a wavelength that is not in a predetermined wavelength band to thereby produce imaging photons having a wavelength that is in said predetermined wavelength band;
detecting said imaging photons with a photon detecting device; and
compensating for receiving said non-Raman scattered photons as a function of the imaging photons and the non-Raman scattered photons to thereby produce a spectrum of the sample.

13. The method of claim 12 wherein the spectrum is a Raman spectrum.

14. The method of claim 12 wherein the spectrum is a spatially accurate wavelength-resolved image.

15. The method of claim 12 wherein the step of compensating for detecting said non-Raman scattered photons further comprises the steps of:
determining the intensity of the non-Raman scattered photons detected by the photon detecting device for each of a plurality of wavelengths; and
for one of the plurality of wavelengths, dividing the intensity of the imaging photons at said one wavelength by the intensity of the non-Raman scattered photons at said one wavelength.

16. The method of claim 12 wherein the step of compensating for detecting said non-Raman scattered photons further comprises the steps of:
determining the intensity of the non-Raman scattered photons detected by the photon detecting device for each of a plurality of wavelengths; and for one of the plurality of wavelengths, subtracting the intensity of the non-Raman scattered photons at said one wavelength from the intensity of the imaging photons at said one wavelength.

17. The method of claim 12 wherein the step of compensating for detecting said non-Raman scattered photons further comprises the steps of:
determining the intensity of the non-Raman scattered photons detected by the photon detecting device for each of a plurality of wavelengths; and
for one of the plurality of wavelengths, mathematically normalizing the intensity of the imaging photons at said one wavelength as a function of the intensity of the non-Raman scattered photons at said one wavelength.

18. The method of claim 12 wherein the step of providing the sample includes providing the sample on a substrate coated with a material that does not emit Raman scattered photons when illuminated by said illuminating photons.

19. The method of claim 18 wherein the step of providing the sample includes providing the sample on a substrate coated with metal.

20. The method of claim 19 wherein the step of providing the sample includes providing the sample on a substrate coated with aluminum.

21. The method of claim 18 wherein the substrate has an optically smooth surface.

22. The method of claim 18 wherein the substrate is a microscope slide.

23. A method for obtaining a corrected spectrum of a sample, the method comprising the steps of:
illuminating the sample with a first light source having a substantially constant intensity at each wavelength of a predetermined wavelength band to thereby obtain a white-light spectral image of the sample;
illuminating the sample with a second light source at each wavelength of the predetermined wavelength band to thereby obtain an initial spectrum of the sample; and
filtering the initial spectrum to substantially remove the white-light spectral image from the initial spectrum to thereby obtain a corrected spectrum of the sample.

24. The method of claim 23 wherein the second light source is a laser light source.

25. The method of claim 23 wherein the spectrum is a Raman spectrum.

26. The method of claim 23 wherein the spectrum is a spatially accurate wavelength-resolved image.

27. The method of claim 23 wherein the step of filtering the initial spectrum further comprises the steps of:
determining the intensity of the white light spectral image for each of a plurality of wavelengths; and
for one of the plurality of wavelengths, dividing the intensity of the initial spectrum at said one wavelength by the intensity of the white light spectral image at said one wavelength.

28. The method of claim 23 wherein the step of filtering the initial spectrum further comprises the steps of:
determining the intensity of the white light spectral image for each of a plurality of wavelengths; and
for one of the plurality of wavelengths, subtracting the intensity of the white light spectral image at said one wavelength from the intensity of the initial spectrum at said one wavelength.

29. The method of claim 23 wherein the step of filtering the initial spectrum further comprises the steps of:
determining the intensity of the white light spectral image for each of a plurality of wavelengths; and for one of the plurality of wavelengths, mathematically normalizing the intensity of the initial spectrum at said one wavelength as a function of the intensity of the white light spectral image at said one wavelength.

30. The method of claim 23 including the step of providing the sample on a substrate coated with a material that does not emit Raman scattered photons when illuminated by said illuminating photons.

31. The method of claim 30 wherein the step of providing the sample includes providing the sample on a substrate coated with metal.

32. The method of claim 31 wherein the step of providing the sample includes providing the sample on a substrate coated with aluminum.

33. The method of claim 30 wherein the substrate has an optically smooth surface.

34. The method of claim 30 wherein the substrate is a microscope slide.

35. A system for producing a spectrum of a sample comprising:
   a sample;
   a photon source for providing illuminating photons;
   an optical device for receiving photons scattered by said sample when illuminated by said illuminating photons to thereby produce collected photons wherein the collected photons include Raman scattered photons and non-Raman scattered photons;
   a tunable filter for receiving said collected photons and passing ones of said collected photons having a wavelength in a predetermined wavelength band to thereby produce imaging photons;
   a photon detecting device for detecting said imaging photons; and
   a processor for compensating for detecting said non-Raman scattered photons as a function of the imaging photons and the non-Raman scattered photons to thereby produce a spectrum of the sample.

36. The system of claim 35 wherein the spectrum is a Raman spectrum.

37. The system of claim 35 wherein the spectrum is a spatially accurate wavelength-resolved image.

38. The system of claim 35 wherein the processor comprises a program for:
   determining the intensity of the non-Raman scattered photons detected by the photon detecting device for each of a plurality of wavelengths; and
   for one of the plurality of wavelengths, dividing the intensity of the imaging photons at said one wavelength by the intensity of the non-Raman scattered photons at said one wavelength.

39. The system of claim 35 wherein the processor comprises a program for:
   determining the intensity of the non-Raman scattered photons detected by the photon detecting device for each of a plurality of wavelengths; and
   for one of the plurality of wavelengths, subtracting the intensity of the non-Raman scattered photons at said one wavelength from the intensity of the imaging photons at said one wavelength.

40. The system of claim 35 wherein the processor comprises a program for:
   determining the intensity of the non-Raman scattered photons detected by the photon detecting device for each of a plurality of wavelengths; and
   for one of the plurality of wavelengths, mathematically normalizing the intensity of the imaging photons at said one wavelength as a function of the intensity of the non-Raman scattered photons at said one wavelength.

41. The system of claim 35 wherein the sample is mounted on a substrate coated with a material that does not emit Raman scattered photons when illuminated by said illuminating photons.

42. The system of claim 41 wherein said substrate is coated with metal.

43. The system of claim 42 wherein said substrate is coated with aluminum.

44. The system of claim 41 wherein the substrate has an optically smooth surface.

45. The system of claim 41 wherein the substrate is a microscope slide.

46. A system for producing a spectrum of a sample comprising:
   a sample;
   a photon source for providing illuminating photons;
   an optical device for receiving photons scattered by said sample when illuminated by said illuminating photons to thereby produce collected photons wherein the collected photons include Raman scattered photons and non-Raman scattered photons;
   a tunable filter for receiving said collected photons and blocking ones of said collected photons having a wavelength that is not in a predetermined wavelength band to thereby produce imaging photons having a wavelength that is in said predetermined wavelength band;
   a photon detecting device for detecting said imaging photons; and
   a processor for compensating for detecting said non-Raman scattered photons as a function of the imaging photons and the non-Raman scattered photons to thereby produce a spectrum of the sample.

47. The system of claim 46 wherein the spectrum is a Raman spectrum.

48. The system of claim 46 wherein the spectrum is a spatially accurate wavelength-resolved image.

49. The system of claim 46 wherein the processor comprises a program for: determining the intensity of the non-Raman scattered photons detected by the photon detecting device for each of a plurality of wavelengths; and
   for one of the plurality of wavelengths, dividing the intensity of the imaging photons at said one wavelength by the intensity of the non-Raman scattered photons at said one wavelength.

50. The system of claim 46 wherein the processor comprises a program for:
   determining the intensity of the non-Raman scattered photons detected by the photon detecting device for each of a plurality of wavelengths; and
   for one of the plurality of wavelengths, subtracting the intensity of the non-Raman scattered photons at said one wavelength from the intensity of the imaging photons at said one wavelength.

51. The system of claim 46 wherein the processor comprises a program for:
   determining the intensity of the non-Raman scattered photons detected by the photon detecting device for each of a plurality of wavelengths; and
   for one of the plurality of wavelengths, mathematically normalizing the intensity of the imaging photons at said one wavelength as a function of the intensity of the non-Raman scattered photons at said one wavelength.

52. The system of claim 46 wherein the sample is mounted on a substrate coated with a material that does not emit Raman scattered photons when illuminated by said illuminating photons.

53. The system of claim 52 wherein said substrate is coated with metal.

54. The system of claim 53 wherein said substrate is coated with aluminum.

55. The system of claim 52 wherein the substrate has an optically smooth surface.

56. The system of claim 52 wherein the substrate is a microscope slide.

57. A system for obtaining a corrected spectrum of a sample, the system comprising:
 a sample;
 a first photon source for illuminating the sample with a first set of photons having a substantially constant intensity at each wavelength of a predetermined wavelength band to thereby obtain a white-light spectral image of the sample;
 a second photon source for illuminating the sample with a second set of photons in said predetermined wavelength band to thereby obtain an initial spectrum of the sample; and
 a processor for filtering the initial spectrum of the sample to substantially remove the white-light spectral image from the initial spectrum to thereby obtain a corrected spectrum of the sample.

58. The system of claim 57 wherein the spectrum is a Raman spectrum.

59. The system of claim 57 wherein the spectrum is a spatially accurate wavelength-resolved image.

60. The system of claim 57 wherein said second photon source is a laser light source.

61. The system of claim 60 wherein the laser light source emits photons having a wavelength in the range of 500-800 nanometers.

62. The system of claim 60 wherein the laser light source emits photons having a wavelength in the range of 280-1200 nanometers.

63. The system of claim 59 wherein the processor comprises a program for:
 determining the intensity of the white light spectral image for each of a plurality of wavelengths; and
 for one of the plurality of wavelengths, dividing the intensity of the initial spectrum at said one wavelength by the intensity of the white light spectral image at said one wavelength.

64. The system of claim 57 wherein the processor comprises a program for:
 determining the intensity of the white light spectral image for each of a plurality of wavelengths; and
 for one of the plurality of wavelengths, subtracting the intensity of the white light spectral image at said one wavelength from the intensity of the initial spectrum at said one wavelength.

65. The system of claim 57 wherein the processor comprises a program for:
 determining the intensity of the white light spectral image for each of a plurality of wavelengths; and
 for one of the plurality of wavelengths, mathematically normalizing the intensity of the initial spectrum at said one wavelength as a function of the intensity of the white light spectral image at said one wavelength.

66. The system of claim 57 wherein the sample is mounted on a substrate coated with a material that does not emit Raman scattered photons when illuminated by said illuminating photons.

67. The system of claim 66 wherein said substrate is coated with metal.

68. The system of claim 67 wherein said substrate is coated with aluminum.

69. The system of claim 66 wherein the substrate has an optically smooth surface.

70. The system of claim 66 wherein the substrate is a microscope slide.

\* \* \* \* \*